United States Patent [19]

Wada et al.

[11] 4,293,199

[45] Oct. 6, 1981

[54] APPARATUS FOR DETECTING ASTIGMATIC AXES AND MEASURING REFRACTIVE POWERS

[75] Inventors: Shinzi Wada; Ikuo Kitao; Yoshinori Oana; Yasuo Kato; Taketoshi Ishihara, all of Tokyo, Japan

[73] Assignee: Tokyo Kogaku Kikai Kakushiki Kaisha, Tokyo, Japan

[21] Appl. No.: 960,056

[22] Filed: Nov. 13, 1978

[30] Foreign Application Priority Data

Nov. 14, 1977 [JP] Japan ................. 52-136488

[51] Int. Cl.³ .............................................. A61B 3/10
[52] U.S. Cl. ........................................ 351/13; 351/14
[58] Field of Search ............... 356/124, 125, 126, 127;
351/13, 14, 6

[56] References Cited

U.S. PATENT DOCUMENTS

| 1,613,658 | 1/1927 | Henker | 351/13 |
| 3,785,723 | 1/1974 | Guyton | 356/127 |
| 4,021,102 | 5/1977 | Iizuka | 351/13 |
| 4,125,320 | 11/1978 | Rassow et al. | 351/13 |

Primary Examiner—John K. Corbin
Assistant Examiner—Rodney Bovernick
Attorney, Agent, or Firm—Stevens, Davis, Miller & Mosher

[57] ABSTRACT

An apparatus for detecting astigmatic axes and measuring refractive powers such as the lens of a human eye. A disc has a first group of slits oriented in one direction and a second group of slits oriented perpendicular thereto. Each slit has a deflecting means with a direction of deflection perpendicular to the lengthwise direction of its slits for measuring the refractive power. The apparatus also has astigmatic axis detecting target means which can be used immediately prior to the refraction so that the refraction on each astigmatic axis can be measured before conditions change in the eye.

4 Claims, 3 Drawing Figures

APPARATUS FOR DETECTING ASTIGMATIC AXES AND MEASURING REFRACTIVE POWERS

The present invention relates to an apparatus for measuring astigmatic axes and refractive powers, and applicable to a refractometer which is adapted to be used for detecting astigmatic axes and measuring refractive powers of a human eye, and to a lensmeter which is adapted to be used for inspecting eyeglass lenses.

A refractometer is generally designed to project an image of a target through the pupil of a patient's eye and to determine the refractive power of the patient's eye from the position of the target wherein the target image is precisely focused on the retina of the eye. The target is usually comprised of a pair of slits which are aligned with each other in the direction of their lengths and a pair of deflecting prisms which are respectively associated with the slits. The pair of prisms function to deflect light bundles through the slits in opposite directions which are perpendicular to the lengthwise axis of the slits. For detection of astigmatic axes, there is provided a further target which is comprised of a pair of radially aligned slits and prisms respectively associated with the slits and having deflecting surfaces inclined in the directions of the lengths of the slits.

When the conventional refractometer is used for eye inspection, the astigmatic axis detecting target image projected on the eye fundus is rotated by means of a suitable optical element such as an image rotator until the slit images are aligned in the lengthwise direction for detecting the angular direction of an astigmatic axis. Then, the refractive power measuring target is moved along the optical axis to determine the refractive power at the astigmatic axis. Thereafter, the astigmatic axis detecting target image is again rotated to detect the other astigmatic axis and a similar operation is repeated to measure the refractive power at this axis. The operation itself is thus troublesome and moreover has a possibility of producing errors in measurement. For example, the refractive powers at the two astigmatic axes are measured successively with a certain difference in time and there may be a possibility that the conditions of self-adjustments of the patient's eye are different between the first and second measurements.

It is therefore an object of the present invention to provide an apparatus for detecting astigmatic axes and measuring refractive powers, which is simple in operation and can provide accurate results.

Another object of the present invention is to provide an apparatus for detecting astigmatic axes and measuring refractive powers, in which the time difference between the first and second measurements can significantly be decreased.

The present invention is applicable not only to a refractometer for inspection of patient's eyes but also to a lensmeter or an ophthalmoscope. The characteristic feature of the present invention is in the structure of the refractive power measuring target which includes a first group of slits oriented in a first direction and a second group of slits oriented in a second direction which is perpendicular to the first direction, each slit being associated with a deflecting element such as a deflecting prism or a diffraction element. In each group, the slits may be parallel with each other or aligned in lengthwise direction and the deflecting elements function to deflect the light bundles which have passed through the slits in directions perpendicular to the lengths of the slits. Where the slits in each group are provided in a pair or pairs, the deflecting elements for such slits in each pair serve to deflect light bundles through the slits in opposite directions.

The target for detecting the astigmatic axes may be of a conventional arrangement as employed in known refractometers. However, it is preferable that the target is comprised of a pair of parallel or aligned slits and another pair of slits which are perpendicular to the first pair of slits, the slits in each pair being associated with deflecting elements for deflecting the light bundles through the slits in directions parallel to the lengths of the slits but opposite to each other.

The refractometer made in accordance with the present invention is very simple in operation. The astigmatic axis detecting target is at first used to determine one of the astigmatic axes and the refractive power measuring target is then projected to measure the refractive power at the one astigmatic axis by finding a position wherein the images of the slits in one group are aligned or in predetermined locations which respect to each other. Thereafter, the refractive power measuring target is simply moved along the optical axis until the images of the slits in the other group are aligned or in predetermined locations with respect to each other to measure the refractive power at the other astigmatic axis. It is therefore possible to perform the first and second measurements in a very short time so that the measurements can be made under substantially the same condition without possibility of producing errors.

Most of existing astigmatic eyes are of normal astigmatism wherein two astigmatic axes are perpendicular with each other. Therefore, the aforementioned procedure is sufficient to accomplish the objects of inspection for astigmatism. Further, where the astigmatic axis detecting target includes four slits which are arranged in a pattern of a cross and respectively associated with deflecting prisms, it is possible to detect an abnormal astigmatism in which two astigmatic axes are not perpendicular with each other.

The above and other objects and features of the present invention will become apparent from the following descriptions of a preferred embodiment taking reference to the accompanying drawings, in which.

Figure 1:
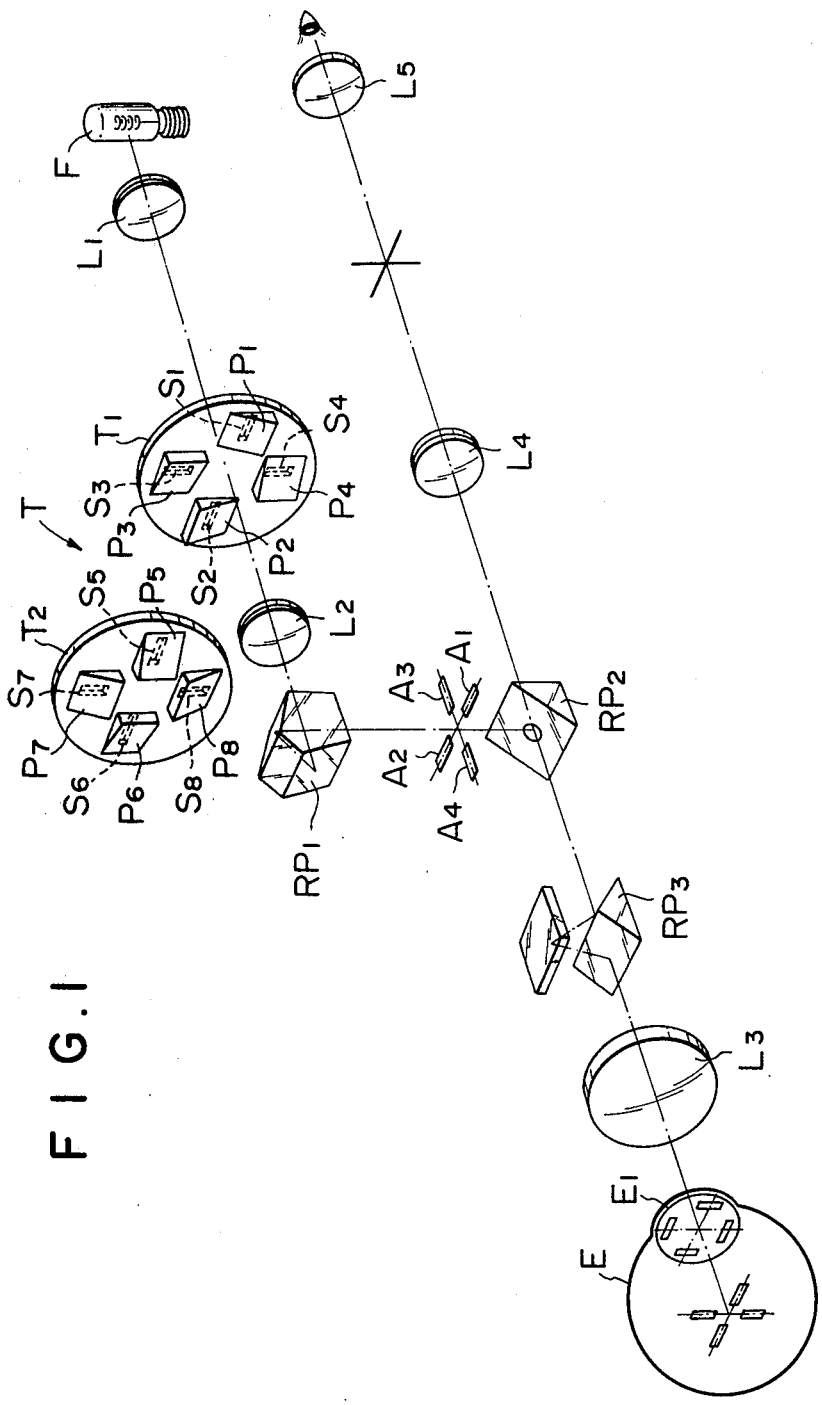
FIG. 1 is a perspective view of an optical system in an eye refractometer in accordance with one embodiment of the present invention.

Referring now to the drawings, particularly to FIG. 1, there is shown diagrammatically an optical system of an eye refractometer in accordance with the present invention. The refractometer includes a projecting optical system and an observing optical system. The projecting optical system is comprised of a light source F, lenses $L_1$ and $L_2$, a pentagonal prism $RP_1$, an apertured prism $RP_2$, an image rotator $RP_3$ and a projecting lens $L_3$ which is adapted to be placed in front of the pupil $E_1$ of a patient's eye E. The pentagonal prism $RP_1$ functions to reflect vertically downwardly the light bundle which has been led from the light source F through the lenses $L_1$ and $L_2$, and the prism $RP_2$ functions to reflect the light from the prism $RP_1$ toward the projecting lens $L_3$.

Between the lenses $L_1$ and $L_2$, there is disposed a target device T which is movable along the optical axis.

The target device T includes a refractive power measuring target $T_1$ and an astigmatic axis detecting target $T_2$. The target $T_1$ has four slits $S_1$, $S_2$, $S_3$ and $S_4$ which are arranged in a pattern of a cross and deflecting prisms $P_1$, $P_2$, $P_3$ and $P_4$ which are respectively associated with the slits $S_1$, $S_2$, $S_3$ and $S_4$. Each of the prisms is so arranged that the direction of deflection is perpendicular to the lengthwise direction of the associated slit so that the direction of deflection in each prism is perpendicular to that of the adjacent prism. Thus, it will be seen that the diametrically opposite prisms $P_1$ and $P_2$ or $P_3$ and $P_4$ have opposite directions of deflection.

The target $T_2$ includes four slits $S_5$, $S_6$, $S_7$ and $S_8$ which are arranged in a pattern of a cross and respectively associated with deflecting prisms $P_5$, $P_6$, $P_7$ and $P_8$ each having a diametrically outwardly directed deflecting angle. These targets $T_1$ and $T_2$ are alternatively inserted into the projecting optical path. It is of course possible to provide such two targets on a single disc so that they are projected simultaneously. It is further possible to project the targets $T_1$ and $T_2$ simultaneously through two separate optical systems.

Between the pentagonal prism $RP_1$ and the apertured prism $RP_2$, there are disposed four apertures $A_1$, $A_2$, $A_3$ and $A_4$ which cooperate with the four slits in each of the targets. The apertures are so located that the image of the light source F is focused through the lens $L_1$, the target T, the lens $L_2$ and the prism $RP_1$ at the apertures $A_1$, $A_2$, $A_3$ and $A_4$. The patient's eye E is positioned so that the pupil $E_1$ thereof is in conjugate with the apertures $A_1$, $A_2$, $A_3$ and $A_4$ with respect to the projecting lens $L_3$. The observing optical system is comprised of lenses $L_4$ and $L_5$ for observing the target image on the eye fundus through the lens $L_3$ and the apertured prism $RP_2$.

Figure 2:
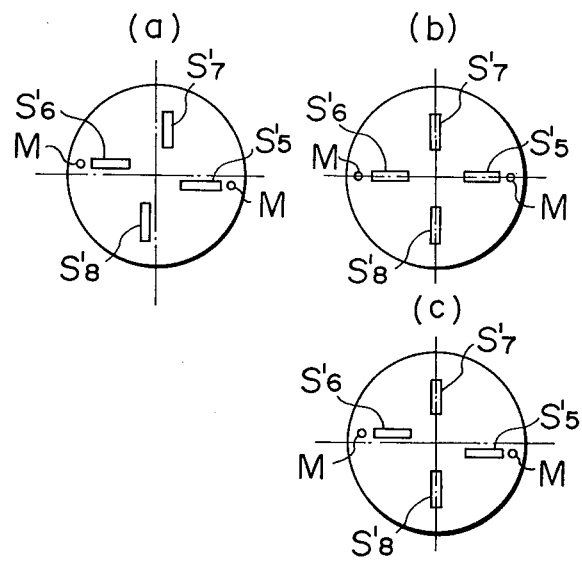
FIG. 2 shows projected images of an astigmatic axis detecting target.

Referring to FIG. 2, there are shown images of target $T_2$ produced on the fundus of the patient's eye. FIG. 2(a) shows an image wherein the lengths of the slits are not coincident with the astigmatic axes. In this position, the image rotator $RP_3$ is actuated to make the lengths of the slits coincide with the astigmatic axes. Where the patient's eye E is of normal astigmatism, the images $S'_5$, $S'_6$, $S'_7$ and $S'_8$ of the slits are produced exactly on crossed lines as shown in FIG. 2(b). However, where the patient's eye E is of abnormal astigmatism, the images of one of the pairs of the slits are offset from the cross line. Thus, it is possible to detect such abnormal astigmatism simultaneously with the astigmatic axes. The image rotator may be omitted and instead the optical system may be made rotatable about the projecting optical axes to obtain the same results.

Figure 3:
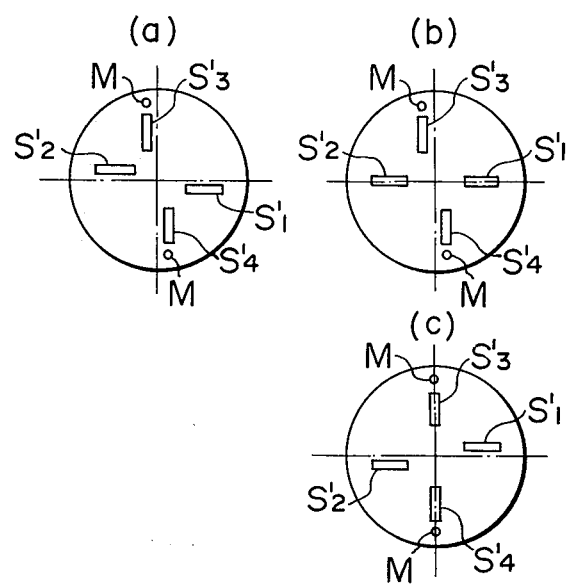
FIG. 3 shows projected images of a refractive power measuring target.

Referring now to FIG. 3, there are shown images of the refractive power measuring target $T_1$ as produced on the eye fundus. Where the target image is in the afocused condition, the images of the slits are offset from the cross line as shown in FIG. 3(a). In this position, the target $T_1$ is moved along the optical axis until the images of one of the pairs of slits are coincided with the cross line as shown, for example, by $S'_1$ and $S'_2$ in FIG. 3(b). The position of the target $T_1$ represents the refractive power at one of the astigmatic axes. Where the patient's eye is of normal astigmatism, the target $T_1$ is again moved along the optical axis until the images of the other pair of slits are coincided with the cross line as shown by $S'_3$ and $S'_4$ in FIG. 3(c) to measure the refractive power at the other astigmatic axis.

Only where the patient's eye is of abnormal astigmatism, the image rotator is actuated after the first measurement of the refractive power to detect the second astigmatic axis. In order to clearly show a specific pair of slits in the astigmatic axis detecting target corresponding to a specific pair of slits in the refractive power measuring target, such slits may be associated with marks such as those shown by M in FIGS. 2 and 3.

The invention has thus been shown and described with reference to a specific embodiment, however, it should be noted that the invention is in no way limited to the details of the illustrated arrangements but changes and modifications may be made without departing from the scope of the appended claims.

We claim:

1. An eye refractometer apparatus for detecting astigmatic axes and measuring refractive powers of a patient's eye, said apparatus comprising refractive power measuring target means including a first group of slits oriented in a first direction and a second group of slits coplanar with the first group of slits and oriented in a second direction which is perpendicular to the first direction, each slit being associated with deflecting means having a direction of deflection perpendicular to the lengthwise direction of that slit, the direction of deflection of the deflecting means for at least one of the slits in each group being opposite to that of the deflecting means for the remainder of the slits in the same group, astigmatic axis detecting target means including at least one group of slits oriented in one direction, each of the slits in the astigmatic axis detecting target means being associated with deflecting means having a direction of deflection parallel with the lengthwise direction of the slit, the direction of deflection of the deflecting means for at least one of the slits in the astigmatic axis detecting target means being opposite to that of the deflecting means for remainder of the slits, means for projecting images of the target means on the retina of the patient's eye along a projecting optical path, means for focusing the projected images, and means for rotating the projected images about the projecting optical path; observing optical means for observing the projected image through the pupil of the patient's eye.

2. Apparatus in accordance with claim 1 in which said astigmatic axis detecting target means includes two perpendicularly oriented pairs of slits, said deflecting means for the slits in the astigmatic axis detecting target means being so located that the direction of deflection of the deflecting means for one of the slits in each pair is opposite to that of the deflecting means for the other of the slits in the pair.

3. Apparatus in accordance with claim 1 in which said rotating means is comprised of an image rotating optical element disposed between the target means and the patient's eye to be inspected.

4. Apparatus in accordance with claim 1 in which said refractive power measuring target means has two perpendicularly oriented pairs of slits, and the direction of deflection of the deflecting means for one of the slits in each pair is opposite to that for the other slit in the same pair.

* * * * *